US006261828B1

(12) United States Patent
Lund

(10) Patent No.: US 6,261,828 B1
(45) Date of Patent: Jul. 17, 2001

(54) PROCESS FOR COMBINED DESIZING AND "STONE-WASHING" OF DYED DENIM

(75) Inventor: Henrik Lund, Copenhagen (DK)

(73) Assignee: Novo Nordisk A/S, Bagsvaerd (DE)

( * ) Notice: Subject to any disclaimer, the term of this patent is extended or adjusted under 35 U.S.C. 154(b) by 0 days.

(21) Appl. No.: 09/069,632

(22) Filed: Apr. 29, 1998

Related U.S. Application Data

(63) Continuation of application No. PCT/DK96/00469, filed on Nov. 15, 1996.

(30) Foreign Application Priority Data

Nov. 15, 1995 (DK) .................................................. 1278/95

(51) Int. Cl.[7] ............................ D06M 16/00; C12N 9/24; C12N 9/28; C11D 3/00; C11D 7/47

(52) U.S. Cl. ......................... 435/263; 435/67.1; 435/200; 435/202; 435/209; 435/252.3; 435/264; 510/303; 510/320; 536/23.2

(58) Field of Search ..................................... 510/303, 320; 435/200, 202, 209, 263, 264, 69.1, 252.3; 536/23.2

(56) References Cited

U.S. PATENT DOCUMENTS

| | | | | |
|---|---|---|---|---|
| 5,460,966 | | 10/1995 | Dixon | 435/263 |
| 5,578,489 | * | 11/1996 | Petersen | 435/263 |
| 5,686,593 | * | 11/1997 | Woldike et al. | 536/23.2 |
| 5,691,295 | * | 11/1997 | Maurer et al. | 510/392 |
| 5,700,676 | * | 12/1997 | Bott et al. | 435/221 |
| 5,700,686 | * | 12/1997 | Foody et al. | 435/263 |
| 5,763,254 | * | 6/1998 | Woldike et al. | 435/209 |
| 5,770,104 | * | 6/1998 | Clarkson et al. | 252/174.12 |
| 5,792,641 | * | 8/1998 | Schulein et al. | 435/209 |
| 5,811,381 | * | 9/1998 | Emalfarb et al | 510/320 |
| 5,888,800 | * | 3/1999 | Wilson et al. | 435/252.31 |

FOREIGN PATENT DOCUMENTS

| | | | |
|---|---|---|---|
| WO 91/17243 | | 11/1991 | (WO) . |
| WO 94/07983 | | 4/1994 | (WO) . |
| WO 95/21247 | | 8/1995 | (WO) . |
| WO 95/24471 | | 9/1995 | (WO) . |
| WO 95/26398 | * | 10/1995 | (WO) . |
| WO 97/282443 | * | 8/1997 | (WO) . |
| WO 97/28256 | * | 8/1997 | (WO) . |

OTHER PUBLICATIONS

Abstract of JP 2080673, Dialog File 351: Derwent WPI Acc. No. 90–129938/199017 (1990).

* cited by examiner

*Primary Examiner*—Ponnathapu Achutamurthy
*Assistant Examiner*—William W. Moore
(74) *Attorney, Agent, or Firm*—Elias J. Lambiris, Esq.; Reza Green, Esq.

(57) ABSTRACT

A one-step process for combined desizing and "stone-washing" of dyed denim, wherein the denim is treated with an amylolytic enzyme in combination with a first abrading monocomponent endoglucanase and a second streak-reducing monocomponent endoglucanase.

20 Claims, 1 Drawing Sheet

PROCESS FOR COMBINED DESIZING AND "STONE-WASHING" OF DYED DENIM

CROSS-REFERENCE TO RELATED APPLICATIONS

Figure 1:
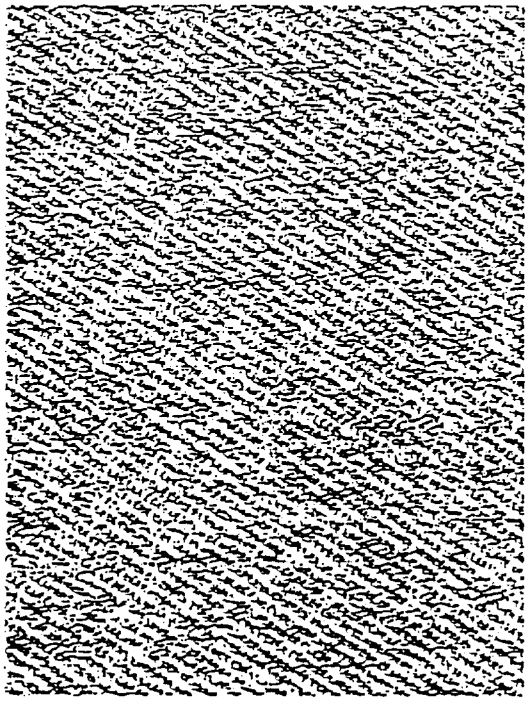

This application is a continuation under 35 U.S.C. 120 of the International application PCT/DK96/00469 filed Nov. 15, 1996 and claims priority under 35 U.S.C. 119 of Danish application 1278/95 filed Nov. 15, 1995, the contents of which are fully incorporated herein by reference.

The present invention relates to a desizing and "stone-washing" one-step process whereby dyed denim having localized variation in colour density of improved uniformity is achieved by treating dyed denim, especially dyed denim garment such as denim jeans, with an amylolytic enzyme and two different endoglucanases in the very same process step.

BACKGROUND OF THE INVENTION

During the weaving of textiles, the threads are exposed to considerable mechanical strain. Prior to weaving on mechanical looms, warp yarns are often coated with size starch or starch derivatives in order to increase their tensile strength and to prevent breaking. The most common sizing agent is starch in native or modified form, yet other polymeric compounds such as polyvinylalcohol (PVA), polyvinylpyrrolidone (PVP), polyacrylic acid (PAA) or derivatives of cellulose (e.g. carboxymethylcellulose (CMC), hydroxyethylcellulose, hydroxypropylcellulose or methylcellulose), may also be abundant in the size.

In general, after the textiles have been woven, the fabric proceeds to a desizing stage, followed by one or more additional fabric processing steps. Desizing is the act of removing size from textiles. After weaving, the size coating must be removed before further processing the fabric in order to ensure a homogeneous and wash-proof result. The preferred method of desizing is enzymatic hydrolysis of the size by the action of amylolytic enzymes.

For the manufacture of denim clothes, the fabric is cut and sown into garments, that is afterwards finished. In particular, for the manufacture of denim garment, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps.

Cotton wax and other lubricants can be applied to yarns in order to increase the speed of cotton weaving. Also waxes of higher melting points are being introduced. Wax lubricants are predominantly triglyceride ester based lubricants. After desizing, the wax either remains or redeposits on the fabric and as a result, the fabric gets darker in shade, gets glossy spots, and becomes more stiff.

International Patent Application No. WO 93/13256 (Novo Nordisk A/S) describes a process for the removal of hydrophobic esters from fabric, in which process the fabric is impregnated during the desizing step with an aqueous solution of lipase. This process has been developed for use in the fabric mills only, and is carried out using existing fabric mill equipment, i.e. a pad roll, a jigger, or a J box.

JP-A 2-80673 discloses a method whereby desizing and softening are achieved by treating cellulose fibres with an aqueous solution containing both amylase and cellulase.

For many years denim jeans manufacturers have washed their garments in a finishing laundry with pumice stones to achieve a soft-hand as well as a desired fashionable "stone-washed" look. This abrasion effect is obtained by locally removing the surface bound dyestuff. Recently cellulytic enzymes have been introduced into the finishing process, turning the stone-washing process into a "bio-stoning process".

The goal of a bio-stoning process is to obtain a distinct, but homogeneous abrasion of the garments (stone-washing appearance). However, uneven stone-washing ("streaks" and "creases") are very frequently occurring. In consequence repair work ("after-painting") is needed on a major part (up to about 80%) of the stone-washed jeans that have been processed in the laundries.

Thus, it is an object of the present invention to provide a process which reduces the problem of streaks and creases on the finished denim garments.

SUMMARY OF THE INVENTION

Accordingly, the present invention provides a process for the treatment of fabrics, which process improves the color distribution/uniformity, stone-wash quality, etc., and which reduces the need for after-painting of the finished clothes.

The invention provides a one-step process for enzymatically desizing and stone-washing dyed denim, which process comprises treating the denim with an amylolytic enzyme, such as an $\alpha$-amylase, in combination with a first abrading monocomponent endoglucanase and a second streak-reducing monocomponent endoglucanase.

DETAILED DESCRIPTION OF THE INVENTION

The present invention provides a process for enzymatic treatment of fabrics, by which process it is possible to provide desized and enzymatically stone-washed dyed denim of improved visual quality.

As described above, enzymatic treatment of fabrics conventionally includes the steps of desizing the fabric by use of amylolytic enzymes, softening the garment (including the steps of bio-polishing, bio-stoning and/or garment wash) by use of cellulytic enzymes, optionally followed by dyeing the garment, washing the garment, and/or softening the garment with a chemical softening agent, typically a cationic, sometimes silicone-based, surface active compound. The process of the present invention may conveniently take place during the desizing and/or softening step of the conventional garment manufacturing steps.

Accordingly, in a preferred embodiment, the process of present invention relates to a one-step process for combined desizing and "stone-washing" of dyed denim, wherein the denim is treated with an amylolytic enzyme, such as an $\alpha$-amylase, in combination with a first abrading monocomponent endoglucanase and a second streak-reducing monocomponent endoglucanase.

In the present context, the term "abrading endoglucanase (or cellulase)" is intended to mean an endoglucanase which is capable of providing the surface of dyed denim fabric (usually sown into garment, especially jeans) localized variations in colour density. Examples of abrading cellulase are those mentioned in the International Patent Application PCT/US89/03274 published as WO 90/02790 which is hereby incorporated by reference.

The term "monocomponent endoglucanase" denotes an endoglucanase which is essentially free from other proteins, in particular other endoglucanases. Monocomponent endoglucanases are typically produced by recombinant techniques, i.e. by cloning and expression of the relevant gene in a homologous or a heterologous host.

In the present context, the term "streak-reducing endoglucanase (or cellulase)" or "levelling" endoglucanase is intended to mean an endoglucanase which is capable of reducing formation of streaks usually present on the surface of dyed denim fabric (usually sown into garment, especially jeans) which has been subjected to a "stone-washing" process, either an enzymatic stone-washing process or process using pumice for providing localized variations in colour density on the denim surface. Examples of streak-reducing or levelling cellulases are those mentioned in the International Patent Application PCT/DK95/00108 published as WO 95/24471 which is hereby incorporated by reference.

The first endoglucanase is preferably a fungal EG V type cellulase. Another useful endoglucanase is a fungal EG III type cellulase obtainable from a strain of the genus Trichoderma. Examples of useful fungal EG III type cellulases are those disclosed in WO 92/06184, WO 93/20208 and WO 93/20209, and WO 94/21801 which are hereby incorporated by reference.

Preferably, the EG V type endoglucanase is derived from or producible by a strain of Scytalidium (f. Humicola), Fusarium, Myceliophthora, more preferably derived from or producible by *Scytalidium thermophilum* (*f. Humicola insolens*), *Fusarium oxysporum* or *Myceliophthora themophila,* most preferably from *Humicola insolens,* DSM 1800, *Fusarium oxysporum,* DSM 2672, or *Myceliophthora themophila,* CBS 117.65.

In one embodiment of the invention, the first endoglucanase is an endoglucanase comprising the amino acid sequence of the *Humicola insolens* endoglucanase shown in SEQ ID No. 1 or is an analogue of said endoglucanase which is at least 60% homologous with the sequence shown in SEQ ID No. 1, reacts with an antibody raised against said endoglucanase, and/or is encoded by a DNA sequence which hybridizes with the DNA sequence encoding said endoglucanase.

In another embodiment of the invention, the first endoglucanase is an endoglucanase comprising the amino acid sequence of the *Fusarium oxysporum* endoglucanase shown in SEQ ID No. 2 or is an analogue of said endoglucanase which is at least 60% homologous with the sequence shown in SEQ ID No. 2, reacts with an antibody raised against said endoglucanase, and/or is encoded by a DNA sequence which hybridizes with the DNA sequence encoding said endoglucanase.

In the present context the homology may be determined as the degree of identity between two or more amino acid sequences by means of computer programs known in the art such as GAP provided in the GCG program package (Needleman and Wunsch, 1970, *Journal of Molecular Biology* 48:443–453). For purposes of determining the degree of identity between two amino acid sequences for the present invention, GAP is used with the following settings: GAP creation penalty of 3.0 and GAP extension penalty of 0.1.

In the present context the antibody reactivity may be determined as follows:

Antibodies to be used in determining immunological cross-reactivity may be prepared by use of the relevant purified enzyme. More specifically, antiserum against the enzyme may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation ($(NH_4)_2SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

The hybridization may be determined by allowing the DNA (or corresponding RNA) sequences to hybridize under the following conditions:

Presoaking of a filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt=s solution (Sambrook et al. 1989), 0.5% SDS and 100 Fg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6–13), $^{32}$P-dCTP-labeled (specific activity>1×10$^9$ cpm/Fg) probe for 12 hours at ca. 45° C. The filter is then washed twice for 30 minutes in 2×SSC, 0.5% SDS at at least 55° C., more preferably at least 60° C., even more preferably at least 65° C., and still more preferably at least 70° C. (high stringency), even more preferably at least 75° C. Molecules to which the oligonucleotide probe hybridizes under these conditions are detected using a x-ray film.

In a preferred embodiment of the process of the invention, the second endoglucanase has a catalytic activity on cellotriose at pH 8.5 corresponding to $k_{cat}$ of at least 0.01 $s^{-1}$, preferably of at least 0.1 $s^{-1}$, more preferably of at least 1 $s^{-1}$.

Preferably, the second endoglucanase is obtainable by or derived from a strain of Humicola, Trichoderma, Myceliophthora, Penicillium, Irpex, Aspergillus, Scytalidium or Fusarium, more preferably from a strain of *Humicola insolens, Fusarium oxysporum* or *Trichoderma reesei.* Preferred second endoglucanases are of the EG I type.

An example of a useful second endoglucanase is an endoglucanase comprising the amino acid sequence of the *Humicola insolens* endoglucanase shown in SEQ ID No. 3 or is an analogue of said endoglucanase which is at least 60% homologous with the sequence shown in SEQ ID No. 3, reacts with an antibody raised against said endoglucanase, and/or is encoded by a DNA sequence which hybridizes with the DNA sequence encoding said endoglucanase.

In the process of the invention, the first and second endoglucanase, respectively, can be used in an amount of corresponding to a cellulase activity between 5 and 8,000 ECU per liter of desizing/@stone-washing@ liquour, preferably between 10 and 5000 ECU per liter of liquor, and more preferably between 50 and 500 ECU per liter of liquor. The first and second endoglucanase, respectively, is preferably dosed in an amount corresponding to 0.01–40 mg endoglucanase/l, more preferably 0.1–2.5 mg/l, especially 0.1–1.25 mg/l.

The substrate of the process of the invention is dyed denim. The denim may be dyed with a natural or a synthetic dye. Examples of synthetic dyes are direct dyes, fiber-reactive dyes or indirect dyes. In a preferred embodiment, the denim is dyed with indigo. Typically, the denim is cut and sown into garment before subjected to the process of the present invention. Examples of garment are jeans, jackets and skirts. An especially preferred example is indigo-dyed denim jeans.

In the process of the invention, conventional desizing enzymes, in particular amylolytic enzymes, can be used in order to remove starch-containing size.

Therefore, an amylolytic enzyme, preferably an α-amylase, may be added during the process of the invention. Conventionally, bacterial α-amylases are used for the desizing, e.g. an α-amylases derived from a strain of Bacillus, particularly a strain of *Bacillus licheniformis,* a strain of *Bacillus amyloliquefaciens,* or a strain of *Bacillus stearothermophilus;* or mutants thereof. Amino acid sequences of such amylases are apparent from, e.g., U.S. Pat. No. 5,928,381. Examples of suitable commercial α-amylase products are TermamylJ, AquazymJ Ultra and AquazymJ (available from Novo Nordisk A/S, Denmark). However, also fungal α-amylases can be used. Examples of fungal α-amylases are those derived from a strain of Aspergillus. Other useful α-amylases are the oxidation-stable α-amylase mutants disclosed in WO 95/21247. For instance, an α-amylase mutant prepared from a parent α-amylase by replacing one or more of the methionine amino acid residues with a Leu, Thr, Ala, Gly, Ser, Ile, Asn, or Asp amino acid residue, preferably a Leu, Thr, Ala, or Gly amino acid residue. Of particular interest is an α-amylase mutant prepared from the *B. licheniformis* α-amylase in which the methionine at position 197 has been replaced with any other amino acid residue, in particular with Leu, Thr, Ala, Gly, Ser, Ile, Asn, or Asp amino acid residue, preferably a Leu, Thr, Ala, or Gly amino acid residue.

The amylolytic enzyme may be added in amounts conventionally used in desizing processes, e.g. corresponding to an α-amylase activity of from about 10 to about 10,000 KNU/l such as from 100 to about 10,000 KNU/l or from 10 to about 5,000 KNU/l. Also, in the process according to the present invention, 1–10 mM of $Ca^{++}$ may be added as a stabilizing agent.

The process of the present invention may be accomplished at process conditions conventionally prevailing in desizing/"stone-washing" processes, as carried out by the person skilled in the art. The process of the invention may, e.g., be carried out batch-wise in a washer extractor.

It is at present contemplated that a suitable liquor/textile ratio may be in the range of from about 20:1 to about 1:1, preferably in the range of from about 15:1 to about 5:1.

In conventional desizing and "stone-washing" processes, the reaction time is usually in the range of from about 1 hour to about 24 hours. However, in the process of the present invention the reaction time may well be less than 1 hour, i.e. from about 5 minutes to about 55 minutes. Preferably the reaction time is within the range of from about 5 or 10 to about 120 minutes.

The pH of the reaction medium greatly depends on the enzyme in question. Preferably the process of the invention is carried out at a pH in the range of from about pH 3 to about pH 11, preferably in the range of from about pH 6 to about pH 9, or within the range of from about pH 5 to about pH 8.

A buffer may be added to the reaction medium to maintain a suitable pH for the enzymes used. The buffer may suitably be a phosphate, borate, citrate, acetate, adipate, triethanolamine, monoethanolamine, diethanolamine, carbonate (especially alkali metal or alkaline earth metal, in particular sodium or potassium carbonate, or ammonium and HCl salts), diamine, especially diaminoethane, imidazole, or amino acid buffer.

The process of the invention may be carried out in the presence of conventional textile finishing agents, including wetting agents, polymeric agents, dispersing agents, etc.

A conventional wetting agent may be used to improve the contact between the substrate and the enzymes used in the process. The wetting agent may be a nonionic surfactant, e.g. an ethoxylated fatty alcohol, an ethoxylated oxo alcohol, an ethoxylated alkyl phenol or an alkoxylated fatty alcohol.

Examples of suitable polymers include proteins (e.g. bovine serum albumin, whey, casein or legume proteins), protein hydrolysates (e.g. whey, casein or soy protein hydrolysate), polypeptides, lignosulfonates, polysaccharides and derivatives thereof, polyethylene glycol, polypropylene glycol, polyvinyl pyrrolidone, ethylene diamine condensed with ethylene or propylene oxide, ethoxylated polyamines, or ethoxylated amine polymers.

The dispersing agent may suitably be selected from nonionic, anionic, cationic, ampholytic or zwitterionic surfactants. More specifically, the dispersing agent may be selected from carboxymethylcellulose, hydroxypropylcellulose, alkyl aryl sulphonates, long-chain alcohol sulphates (primary and secondary alkyl sulphates), sulphonated olefins, sulphated monoglycerides, sulphated ethers, sulphosuccinates, sulphonated methyl ethers, alkane sulphonates, phosphate esters, alkyl isothionates, acylsarcosides, alkyltaurides, fluorosurfactants, fatty alcohol and alkylphenol condensates, fatty acid condensates, condensates of ethylene oxide with an amine, condensates of ethylene oxide with an amide, sucrose esters, sorbitan esters, alkyloamides, fatty amine oxides, ethoxylated monoamines, ethoxylated diamines, alcohol ethoxylate and mixtures thereof.

In another preferred embodiment of the invention, the process may be performed using a lipolytic enzyme that is capable of carrying out lipolysis at elevated temperatures. In order to efficiently hydrolyse hydrophobic esters of high melting points, lipolytic enzymes that possess sufficient thermostability and lipolytic activity at temperatures of about 60 EC or above, are preferred. Adequate hydrolysis can be obtained even above or below the optimum temperature of the lipolytic enzyme by increasing the enzyme dosage.

The lipolytic enzyme may be of animal, plant or microbial origin. Examples of microorganisms producing such thermostable lipolytic enzymes are strains of Humicola, preferably a strain of *Humicola brevispora,* a strain of *Humicola lanuginosa,* a strain of *Humicola brevis* var. *thermoidea,* a strain of *Humicola insolens,* a strain of Fusarium, preferably a strain of *Fusarium oxysporum,* a strain of Rhizomucor, preferably a strain of *Rhizomucor miehei,* a strain of Chromobacterium, preferably a strain of *Chromobacterium viscosum,* and a strain of Aspergillus, preferably a strain of *Aspergillus niger.* Preferred thermostable lipolytic enzymes are derived from strains of Candida or Pseudomonas, particularly a strain of *Candida antarctica,* a strain of *Candida tsukubaensis,* a strain of *Candida auriculariae,* a strain of *Candida humicola,* a strain of *Candida foliarum,* a strain of *Candida cylindracea* (also called *Candida rugosa*), a strain of *Pseudomonas cepacia,* a strain of *Pseudomonas fluorescens,* a strain of *Pseudomonas fragi,* a strain of *Pseudomonas stutzeri,* or a strain of *Thermomyces lanuginosus.*

Lipolytic enzymes from strains of *Candida antarctica* and *Pseudomonas cepacia* are preferred, in particular lipase A from *Candida antarctica.* Such lipolytic enzymes, and methods for their production, are known from e.g. WO 88/02775, U.S. Pat. No. 4,876,024, and WO 89/01032, which publications are hereby included by reference.

The enzyme dosage is dependent upon several factors, including the enzyme in question, the desired reaction time, the temperature, the liquid/textile ratio, etc. It is at present contemplated that the lipolytic enzyme may be dosed in an amount corresponding to of from about 0.01 to about 10,000 KLU/l, preferably of from about 0.1 to about 1000 KLU/l.

Conventional finishing agents that may be present in a process of the invention include, but are not limited to pumice stones and perlite. Perlite is a naturally occurring volcanic rock. Preferably, heat expanded perlite may be used. The heat expanded perlite may e.g. be present in an amount of 20–95 w/w % based on the total weight of the composition.

Cellulytic Activity

The cellulytic activity may be measured in endo-cellulase units (ECU), determined at pH 7.5, with carboxymethyl cellulose (CMC) as substrate.

The ECU assay quantifies the amount of catalytic activity present in the sample by measuring the ability of the sample to reduce the viscosity of a solution of carboxymethylcellulose (CMC). The assay is carried out at 40 EC; pH 7.5; 0.1M phosphate buffer; time 30 min; using a relative enzyme standard for reducing the viscosity of the CMC Hercules 7 LFD substrate; enzyme concentration approx. 0.15 ECU/ml. The arch standard is defined to 8200 ECU/g.

Amylolytic Activity

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue colour is formed, but during the break-down of the starch the blue colour gets weaker and gradually turns into a reddish-brown, which is compared to a coloured glass standard.

One Kilo Novo alfa Amylase Unit (KNU) is defined as the amount of enzyme which, under standard conditions (i.e. at 37° C.±0.05; 0.0003 M $Ca^{2+}$; and pH 5.6) dextrinizes 5.26 g starch dry substance Merck Amylum solubile.

A folder AF 9/6 describing this analytical method in more detail is available upon request to Novo Nordisk A/S, Denmark, which folder is hereby included by reference.

Lipolytic Activity

The lipolytic activity may be determined using tributyrine as substrate. This method is based on the hydrolysis of tributyrin by the enzyme, and the alkali consumption is registered as a function of time.

One Lipase Unit (LU) is defined as the amount of enzyme which, under standard conditions (i.e. at 30.0° C.; pH 7.0; with Gum Arabic as emulsifier and tributyrine as substrate) liberates 1 :mol titrable butyric acid per minute (1 KLU=1000 LU).

A folder AF 95/5 describing this analytical method in more detail is available upon request to Novo Nordisk A/S, Denmark, which folder is hereby included by reference.

EXAMPLE 1

The following example illustrates the effect of adding a streak-reducing or levelling endoglucanase to the combined desizing-abrasion process in order to reduce the number of streaks on denim jeans or other garment and to produce denim garment, especially jeans, with a uniformly localized color variation.

Wash trials were carried out under the following conditions:

Textile:

Blue denim DAKOTA, 142 oz, 100% cotton. The denim was cut and sewed into "legs" of approximately 37.5×100 cm (about 375 g each). Two new legs and one old (used one time) leg were used in each trial (a total of approx. 1100 g textile).

Enzyme:

Trial A: Amylase: Termamyl[7], dosage: 200 KNU/l Endoglucanase (cellulase): EG V (a monocomponent ~43 kD endoglucanase from *Humicola insolens,* DSM 1800, having the amino acid sequence of SEQ ID No. 1), dosage: 10 ECU/g denim Trial B: Amylase: Termamyl[7], dosage: 200 KNU/l Endoglucanase (cellulase): EG V (as in trial A), dosage: 10 ECU/g denim EG I (monocomponent endoglucanase from *Humicola insolens,* DSM 1800, having the amino acid sequence of SEQ ID No. 3), dosage: 10 ECU/g denim Washing was carried out in a wascator (FOM71 LAB). Wash-program:

1) Main wash at 55° C., 20 l water, 120 min, buffer and enzyme added.
   Buffer: 30 g $KH_2PO_4$+20 g $Na_2HPO_4$, pH7
2) Drain 30 sec.
3) Rinse at 80° C., normal action, 32 l water, min.; 20 g $Na_2CO_3$ added
4) Drain 30 sec.
5) Rinse at 54° C., normal action, 32 l water, 5 min.
6) Drain 30 sec.
7) Rinse at 14° C., normal action, 32 l water, 5 min.
8) Drain 30 sec.
9) Spinning 40 sec. at low speed and 50 sec. at high speed.

Drying: The samples were dried in a tumble-dryer. The jeans from the two trials were abraded to almost the same level.

Evaluation:

5 persons skilled in the art of evaluating denim were asked to grade the denim legs (two legs from each trial, leg "1" and "3" from trial B, leg "2" and "4" from trial A) from 1 to 4, where 1 was the least streaked denim leg and 4 was the leg with most streaks on.

Grading were as shown in the table below:

| | Person 1 | Person 2 | Person 3 | Person 4 | Person 5 |
|---|---|---|---|---|---|
| Grade 1 | 1 | 3 | 3 | 3 | 3 |
| Grade 2 | 3 | 1 | 1 | 1 | 1 |
| Grade 3 | 4 | 2 | 2 | 2 | 2 |
| Grade 4 | 2 | 4 | 4 | 4 | 4 |

As can be seen from the table, the denim legs treated in the combi-process of the invention with a combination of two monocomponent endoglucanases having abrading and strak-reducing properties, respectively, e.g. an EG V type and EG I type cellulase, are all rated to have the best appearance with respect to streaking and uniformity of the localized color variation.

Figure 2:
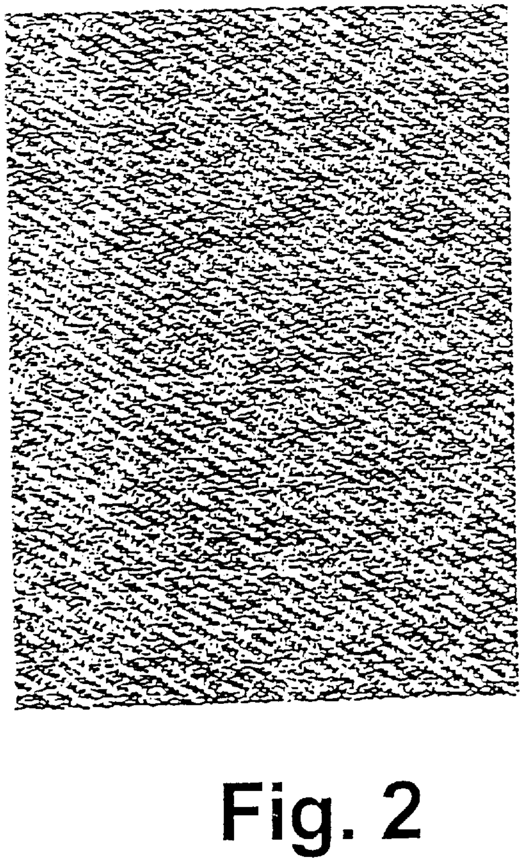

FIGS. 1 and 2:

To illustrate the change in uniformity that can be obtained by using a streak-reducing or levelling endoglucanse (cellulase) in the process of the invention, swatches from trial A and B were scanned (HP ScanJet II CX) into a computer and printed in black-and-white.

FIG. 1 show part of a denim leg from trial B and FIG. 2 show part of a denim leg from trial A.

What is claimed is:

1. A one-step process for combining desizing and "stone-washing" of dyed denim, said process comprising treating the denim with (i) an amylolytic enzyme (ii) an abrading monocomponent endoglucanase, and (iii) a streak-reducing monocomponent endoglucanase.

2. The process according to claim 1, wherein the amylolytic enzyme is an α-amylase.

3. The process according to claim 2, wherein the α-amylase is derived from the bacterium Bacillus or from the fungus Aspergillus.

4. The process according to claim 2, wherein the α-amylase is derived from a species selected from the group consisting of *Bacillus licheniformis, Bacillus amyloliquefaciens, Bacillus subtilis Bacillus stearothermophilus* and mutants of any of the forgoing.

5. The process according to claim 4, wherein the α-amylase is selected from the oxidation-stable α-amylase mutants disclosed in U.S. Pat. No. 5,928,381.

6. The process according to claim 1, wherein the abrading endoglucanase is a fungal EG V cellulase or a fungal EG III cellulase derived from a species of the genus Trichoderma.

7. The process according to claim 6, wherein the EG V endoglucanase is derived from a genus selected from the group consisting of Scytalidium (f. Humicola), Fusarium, and Myceliophthora.

8. The process according to claim 7, wherein the EG V endoglucanase is derived from a species selected from the group consisting of *Soytalidium thermophilum* (f. *Humicola insolens*), *Fusarium oxysporum* and *Myceltophthora themophila*.

9. The process according to claim 8, wherein the endoglucanase comprises an amino acid sequence selected from the group consisting of i) SEQ ID NO 1, and ii) an amino acid sequence encoded by a DNA sequence which hybridizes under stringent conditions with the DNA sequence encoding SEQ ID NO:1.

10. The process according to claim 8, wherein the endoglucanase comprises an amino acid sequence selected from the group consisting of i) SEQ ID NO:2, and ii) an amino acid sequence encoded by a DNA sequence which hybridizes under stringent conditions with the DNA sequence encoding SEQ ID NO:2.

11. The process according to claim 1, wherein the streak-reducing endoglucanase has a catalytic activity on cellotriose at pH 8.5 corresponding to $k_{cat}$ of at least 0.01 $s^{-1}$.

12. The process according to claim 11, wherein the streak-reducing endoglucanase is derived from a species selected from the group consisting of Humicola, Trichoderma, Myceliophthora, Penicillium, Irpex, Aspergillus, Scytalidium and Fusarium.

13. The process according to claim 12, wherein the endoglucanase is derived from a species selected from the group consisting of *Humicola insolens, Fusarium oxysporum* and *Trichoderma reesei.*

14. The process according to claim 12, wherein the endoglucanase comprises an amino acid sequence of the endoglucanase selected from the group consisting of i) SEQ ID NO:3, and ii) an amino acid sequence encoded by a DNA sequence which hybridizes under stringent conditions with the DNA sequence encoding SEQ ID NO:3.

15. The process according to claim 1, wherein the abrading and streak-reducing endoglucanase are each used in an amount corresponding to a cellulase activity between 5 and 8000 ECU per liter of desizing/"stone-washing" liquor.

16. The process according to claim 1, wherein the treatment is performed at a temperature in the range of 30–100° C. and a pH in the range of 3–11.

17. The process according to claim 1, wherein denim is dyed with a natural dye or a synthetic dye.

18. The process according to claim 1, further comprising treating the denim with a thermostable lipolytic enzyme.

19. The process according to claim 18, wherein the lipolytic enzyme is present in an amount of from about 0.01 to about 10,000 KLU/l.

20. The process according to claim 1, wherein the α-amylase is present in an amount of from about 100 to about 10,000 KNU/l.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
(A) LENGTH: 415 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:1:

```
Gln Lys Pro Gly Glu Thr Lys Glu Val His Pro Gln Leu Thr Thr Phe
  1               5                  10                  15

Arg Cys Thr Lys Arg Gly Gly Cys Lys Pro Ala Thr Asn Phe Ile Val
            20                  25                  30

Leu Asp Ser Leu Ser His Pro Ile His Arg Ala Glu Gly Leu Gly Pro
        35                  40                  45

Gly Gly Cys Gly Asp Trp Gly Asn Pro Pro Pro Lys Asp Val Cys Pro
    50                  55                  60

Asp Val Glu Ser Cys Ala Lys Asn Cys Ile Met Glu Gly Ile Pro Asp
65                  70                  75                  80

Tyr Ser Gln Tyr Gly Val Thr Thr Asn Gly Thr Ser Leu Arg Leu Gln
                85                  90                  95

His Ile Leu Pro Asp Gly Arg Val Pro Ser Pro Arg Val Tyr Leu Leu
            100                 105                 110

Asp Lys Thr Lys Arg Arg Tyr Glu Met Leu His Leu Thr Gly Phe Glu
        115                 120                 125

Phe Thr Phe Asp Val Asp Ala Thr Lys Leu Pro Cys Gly Met Asn Ser
    130                 135                 140

Ala Leu Tyr Leu Ser Glu Met His Pro Thr Gly Ala Lys Ser Lys Tyr
145                 150                 155                 160

Asn Pro Gly Gly Ala Tyr Tyr Gly Thr Gly Tyr Cys Asp Ala Gln Cys
                165                 170                 175

Phe Val Thr Pro Phe Ile Asn Gly Leu Gly Asn Ile Glu Gly Lys Gly
            180                 185                 190

Ser Cys Cys Asn Glu Met Asp Ile Trp Glu Ala Asn Ser Arg Ala Ser
        195                 200                 205

His Val Ala Pro His Thr Cys Asn Lys Lys Gly Leu Tyr Leu Cys Glu
    210                 215                 220

Gly Glu Glu Cys Ala Phe Glu Gly Val Cys Asp Lys Asn Gly Cys Gly
225                 230                 235                 240

Trp Asn Asn Tyr Arg Val Asn Val Thr Asp Tyr Tyr Gly Arg Gly Glu
                245                 250                 255

Glu Phe Lys Val Asn Thr Leu Lys Pro Phe Thr Val Val Thr Gln Phe
            260                 265                 270

Leu Ala Asn Arg Arg Gly Lys Leu Glu Lys Ile His Arg Phe Tyr Val
        275                 280                 285

Gln Asp Gly Lys Val Ile Glu Ser Phe Tyr Thr Asn Lys Glu Gly Val
    290                 295                 300

Pro Tyr Thr Asn Met Ile Asp Asp Glu Phe Cys Glu Ala Thr Gly Ser
305                 310                 315                 320
```

-continued

```
Arg Lys Tyr Met Glu Leu Gly Ala Thr Gln Gly Met Gly Glu Ala Leu
                325                 330                 335

Thr Arg Gly Met Val Leu Ala Met Ser Ile Trp Trp Asp Gln Gly Gly
            340                 345                 350

Asn Met Glu Trp Leu Asp His Gly Glu Ala Gly Pro Cys Ala Lys Gly
        355                 360                 365

Glu Gly Ala Pro Ser Asn Ile Val Gln Val Glu Pro Phe Pro Glu Val
    370                 375                 380

Thr Tyr Thr Asn Leu Arg Trp Gly Glu Ile Gly Ser Thr Tyr Gln Glu
385                 390                 395                 400

Val Gln Lys Pro Lys Pro Lys Pro Gly His Gly Pro Arg Ser Asp
                405                 410                 415
```

(2) INFORMATION FOR SEQ ID NO:2:

(i) SEQUENCE CHARACTERISTICS:
(A) LENGTH: 409 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

```
Gln Thr Pro Asp Lys Ala Lys Glu Gln His Pro Lys Leu Glu Thr Tyr
1               5                   10                  15

Arg Cys Thr Lys Ala Ser Gly Cys Lys Lys Gln Thr Asn Tyr Ile Val
            20                  25                  30

Ala Asp Ala Gly Ile His Gly Ile Arg Arg Ser Ala Gly Cys Gly Asp
        35                  40                  45

Trp Gly Gln Lys Pro Asn Ala Thr Ala Cys Pro Asp Glu Ala Ser Cys
    50                  55                  60

Ala Lys Asn Cys Ile Leu Ser Gly Met Asp Ser Asn Ala Tyr Lys Asn
65                  70                  75                  80

Ala Gly Ile Thr Thr Ser Gly Asn Lys Leu Arg Leu Gln Gln Leu Ile
                85                  90                  95

Asn Asn Gln Leu Val Ser Pro Arg Val Tyr Leu Leu Glu Glu Asn Lys
            100                 105                 110

Lys Lys Tyr Glu Met Leu His Leu Thr Gly Thr Glu Phe Ser Phe Asp
        115                 120                 125

Val Glu Met Glu Lys Leu Pro Cys Gly Met Asn Gly Ala Leu Tyr Leu
    130                 135                 140

Ser Glu Met Pro Gln Asp Gly Gly Lys Ser Thr Ser Arg Asn Ser Lys
145                 150                 155                 160

Ala Gly Ala Tyr Tyr Gly Ala Gly Tyr Cys Asp Ala Gln Cys Tyr Val
                165                 170                 175

Thr Pro Phe Ile Asn Gly Val Gly Asn Ile Lys Gly Gln Gly Val Cys
            180                 185                 190

Cys Asn Glu Leu Asp Ile Trp Glu Ala Asn Ser Arg Ala Thr His Ile
        195                 200                 205

Ala Pro His Pro Cys Ser Lys Pro Gly Leu Tyr Gly Cys Thr Gly Asp
    210                 215                 220

Glu Cys Gly Ser Ser Gly Ile Cys Asp Lys Ala Gly Cys Gly Trp Asn
225                 230                 235                 240

His Asn Arg Ile Asn Val Thr Asp Phe Tyr Gly Arg Gly Lys Gln Tyr
                245                 250                 255
```

-continued

```
Lys Val Asp Ser Thr Arg Lys Phe Thr Val Thr Ser Gln Phe Val Ala
            260                 265                 270

Asn Lys Gln Gly Asp Leu Ile Glu Leu His Arg His Tyr Ile Gln Asp
        275                 280                 285

Asn Lys Val Ile Glu Ser Ala Val Val Asn Ile Ser Gly Pro Pro Lys
    290                 295                 300

Ile Asn Phe Ile Asn Asp Lys Tyr Cys Ala Ala Thr Gly Ala Asn Glu
305                 310                 315                 320

Tyr Met Arg Leu Gly Gly Thr Lys Gln Met Gly Asp Ala Met Ser Arg
                325                 330                 335

Gly Met Val Leu Ala Met Ser Val Trp Trp Ser Glu Gly Asp Phe Met
            340                 345                 350

Ala Trp Leu Asp Gln Gly Val Ala Gly Pro Cys Asp Ala Thr Glu Gly
        355                 360                 365

Asp Pro Lys Asn Ile Val Lys Val Gln Pro Asn Pro Glu Val Thr Phe
    370                 375                 380

Ser Asn Ile Arg Ile Gly Glu Ile Gly Ser Thr Ser Ser Val Lys Ala
385                 390                 395                 400

Pro Ala Tyr Pro Gly Pro His Arg Leu
                405
```

(2) INFORMATION FOR SEQ ID NO:3:

(i) SEQUENCE CHARACTERISTICS:
(A) LENGTH: 435 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:3:

```
Met Ala Arg Gly Thr Ala Leu Leu Gly Leu Thr Ala Leu Leu Leu Gly
  1               5                  10                  15

Leu Val Asn Gly Gln Lys Pro Gly Glu Thr Lys Glu Val His Pro Gln
             20                  25                  30

Leu Thr Thr Phe Arg Cys Thr Lys Arg Gly Gly Cys Lys Pro Ala Thr
         35                  40                  45

Asn Phe Ile Val Leu Asp Ser Leu Ser His Pro Ile His Arg Ala Glu
     50                  55                  60

Gly Leu Gly Pro Gly Gly Cys Gly Asp Trp Gly Asn Pro Pro Pro Lys
 65                  70                  75                  80

Asp Val Cys Pro Asp Val Glu Ser Cys Ala Lys Asn Cys Ile Met Glu
                 85                  90                  95

Gly Ile Pro Asp Tyr Ser Gln Tyr Gly Val Thr Thr Asn Gly Thr Ser
            100                 105                 110

Leu Arg Leu Gln His Ile Leu Pro Asp Gly Arg Val Pro Ser Pro Arg
        115                 120                 125

Val Tyr Leu Leu Asp Lys Thr Lys Arg Arg Tyr Glu Met Leu His Leu
    130                 135                 140

Thr Gly Phe Glu Phe Thr Phe Asp Val Asp Ala Thr Lys Leu Pro Cys
145                 150                 155                 160

Gly Met Asn Ser Ala Leu Tyr Leu Ser Glu Met His Pro Thr Gly Ala
                165                 170                 175

Lys Ser Lys Tyr Asn Ser Gly Gly Ala Tyr Tyr Gly Thr Gly Tyr Cys
            180                 185                 190
```

-continued

```
Asp Ala Gln Cys Phe Val Thr Pro Phe Ile Asn Gly Leu Gly Asn Ile
        195                 200                 205

Glu Gly Lys Gly Ser Cys Cys Asn Glu Met Asp Ile Trp Glu Val Asn
    210                 215                 220

Ser Arg Ala Ser His Val Val Pro His Thr Cys Asn Lys Lys Gly Leu
225                 230                 235                 240

Tyr Leu Cys Glu Gly Glu Glu Cys Ala Phe Glu Gly Val Cys Asp Lys
                245                 250                 255

Asn Gly Cys Gly Trp Asn Asn Tyr Arg Val Asn Val Thr Asp Tyr Tyr
            260                 265                 270

Gly Arg Gly Glu Glu Phe Lys Val Asn Thr Leu Lys Pro Phe Thr Val
        275                 280                 285

Val Thr Gln Phe Leu Ala Asn Arg Arg Gly Lys Leu Glu Lys Ile His
    290                 295                 300

Arg Phe Tyr Val Gln Asp Gly Lys Val Ile Glu Ser Phe Tyr Thr Asn
305                 310                 315                 320

Lys Glu Gly Val Pro Tyr Thr Asn Met Ile Asp Asp Glu Phe Cys Glu
                325                 330                 335

Ala Thr Gly Ser Arg Lys Tyr Met Glu Leu Gly Ala Thr Gln Gly Met
            340                 345                 350

Gly Glu Ala Leu Thr Arg Gly Met Val Leu Ala Met Ser Ile Trp Trp
        355                 360                 365

Asp Gln Gly Gly Asn Met Glu Trp Leu Asp His Gly Glu Ala Gly Pro
    370                 375                 380

Cys Ala Lys Gly Glu Gly Ala Pro Ser Asn Ile Val Gln Val Glu Pro
385                 390                 395                 400

Phe Pro Glu Val Thr Tyr Thr Asn Leu Arg Trp Gly Glu Ile Gly Ser
                405                 410                 415

Thr Tyr Gln Glu Val Gln Lys Pro Lys Pro Lys Pro Gly His Gly Pro
            420                 425                 430

Arg Ser Asp
        435
```